United States Patent [19]
Yagihara et al.

[11] 4,121,934
[45] Oct. 24, 1978

[54] SILVER HALIDE PHOTOGRAPHIC LIGHT-SENSITIVE MATERIAL

[75] Inventors: Morio Yagihara; Mitsugu Tanaka; Toshiaki Aono; Takeshi Hirose, all of Minami-ashigara, Japan

[73] Assignee: Fuji Photo Film Co., Ltd., Minami-ashigara, Japan

[21] Appl. No.: 813,608

[22] Filed: Jul. 7, 1977

[30] Foreign Application Priority Data

Jul. 7, 1976 [JP] Japan .................. 51-81141

[51] Int. Cl.$^2$ .................. G03C 7/16; G03C 1/76
[52] U.S. Cl. .................. 96/22; 96/66.3; 96/74; 96/95; 96/100 R
[58] Field of Search .................. 96/22, 66.3, 74, 95, 96/100

[56] References Cited

U.S. PATENT DOCUMENTS

| | | |
|---|---|---|
| 3,632,345 | 1/1972 | Marx et al. .................. 96/95 |
| 3,756,821 | 9/1973 | Hayashi et al. .................. 96/55 |
| 3,933,500 | 1/1976 | Shiba et al. .................. 96/74 |
| 4,015,989 | 4/1977 | Oishi et al. .................. 96/74 |
| 4,029,503 | 6/1977 | Fujiwhara et al. .................. 96/66.3 |
| 4,049,455 | 9/1977 | Kikuchi et al. .................. 96/95 |

Primary Examiner—J. Travis Brown
Attorney, Agent, or Firm—Sughrue, Rothwell, Mion, Zinn and Macpeak

[57] ABSTRACT

A photographic light-sensitive material comprising a support having thereon at least one silver halide emulsion layer containing a coupling compound which forms a colorless compound with oxidized developer, said coupling compound having the formula

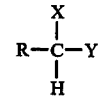

wherein R, X and Y are defined in the specification.

33 Claims, 2 Drawing Figures

- PC: PROTECTIVE LAYER
- BL: BLUE-SENSITIVE EMULSION LAYER
- YF: YELLOW FILTER LAYER
- GL: GREEN-SENSITIVE EMULSION LAYER
- $ML_1$: INTERMEDIATE LAYER
- RL: RED-SENSITIVE EMULSION LAYER
- $ML_2$: INTERMEDIATE LAYER
- AHL: ANTIHALATION LAYER
- SUPPORT $\Delta D^G = D_1^G - D_2^G$

SILVER HALIDE PHOTOGRAPHIC LIGHT-SENSITIVE MATERIAL

BACKGROUND OF THE INVENTION

1. Field of the Invention

The present invention relates to a silver halide photographic light-sensitive material containing a novel non-color forming coupling compound capable of releasing a development inhibitor.

2. Description of the Prior Art

It is known that a compound capable of releasing a development inhibitor can be used by addition of such a compound to a photographic light-sensitive material or a processing solution. The use of such a compound provides an image having improved quality where the compound imagewise releases a development inhibitor with a moderate development inhibiting action at a certain step between exposure and development of a photographic light-sensitive material. On the other hand, when such a compound releases a development inhibitor capable of completely inhibiting development, the compound provides a reversal image of improved quality. Such compounds can be employed for preparing both black-and-white light-sensitive materials and color light-sensitive materials, and have found a wide variety of applications, for example, to improve the quality of an image which a conventional color light-sensitive material provides, in application to light-sensitive materials for special uses such as light-sensitive materials with a wide latitude or for forming double images, for the formation of reversal images, to provide a masking effect by the combined use of a fogged emulsion and such a compound, for the production of color diffusion transfer photographic materials and color direct positive photographic light-sensitive materials and the like.

It has been found by a number of researchers that compounds of this type can contribute to an improvement in image quality because a development inhibitor is released imagewise by the reaction of the oxidation product of a color developing agent with a compound of this type when a multi-layer color light-sensitive material containing such a compound in a light-sensitive layer thereof is exposed to light and then developed with a color developer to exert effects on layers adjacent the light-sensitive layer. That is, the development inhibitor can provide not only a so-called intralayer effect to achieve controlled contrast, reduced graininess and improved sharpness of the developed image, and the like, but also a so-called interlayer effect such as preventing color turbidity and improved color purity due to a masking effect, and the like. Typical development inhibitor releasing compounds of this type include the so-called DIR couplers, the active position of which contains a group which exhibits a development inhibiting action when it is split from the active position of the coupler compound. DIR couplers form dyes by coupling with the oxidation product of a color developing agent and release a development inhibitor. Compounds such as those disclosed in U.S. Pat. Nos. 3,227,554, 3,701,783, 3,615,506, 3,617,291 and the like are known as DIR couplers. DIR couplers are used for the purpose of controlling the image tone, reducing the graininess of the image, improving color reproduction and the like, as is well known from the disclosure in the above described patents.

However, in many cases, DIR couplers of this type do not exert the desired inhibiting effect because the dye yield upon development adversely affects color reproduction unless an appropriate type of a coupler residue and an appropriate amount of the coupler are precisely chosen and convenient selection of a coupler residue for color reproduction restricts the permissible reactivity of the oxidation product of the color developing agent and the coupler. In addition, DIR couplers of this type have various disadvantages such as poor stability against ageing, they often exhibit a desensitization effect, they produce mottle resulting from contamination of the developer solution and the like.

The so-called non-color forming type of coupling compounds were developed with the intention of eliminating these disadvantages, which coupling compounds yield essentially colorless products or colored products whose colors are changed, however, and become essentially colorless in the course of photographic treatment upon coupling with the oxidation product of a color developing agent, and also yield a development inhibitor at the same time. Known compounds of this type include compounds such as are disclosed in German Patent Publication (DAS) No. 1,547,640, German Patent Application (OLS) No. 2,362,752, and the like. While these compounds have advantageous properties they also have some drawbacks. One drawback is the formation of a compound which causes stain. Such a compound is formed by the coupling reaction of the so-called non-color forming type coupling compound with the oxidation product of the color developer. Their most serious drawback, however, is the low reactivity of coupling compounds of this type with oxidation products of color developing agents. Accordingly, a large amount of these compounds must be employed because of their low reactivity and this results in a reduction in photographic characteristics and a decrease in shelf life. Further, all compounds disclosed in the above-described patent references yield mercapto group-containing compounds by reacting with the oxidation product of a developing agent. When compounds of this type are employed for producing a multilayer color photographic light-sensitive material, the resulting development inhibiting agent tends to remain in the layer to which such compound was added, i.e., it diffuses only with difficulty into other layers. Therefore, these compounds contribute only slightly to the so-called interlayer effect, resulting in unsatisfactory color correction.

In order to improve these drawbacks, a compound in which a triazole ring or a diazole ring is bonded to the coupling position through the nitrogen atom at the 1-position as described in Japanese Patent Application (OPI) No. 122,335/74 corresponding to U.S. Pat. No. 3,933,500 and German Patent Application (OLS) No. 2,414,006 is provided. While the photographic properties are improved to a certain extent using this approach, it is desirable from a practical standpoint to further improve these properties.

SUMMARY OF THE INVENTION

A first object of the present invention is to provide a novel non-color forming coupling compound.

A second object of the present invention is to provide a non-color forming coupling compound which rapidly reacts with the oxidation product of a developing agent to result in the release of a compound with a development inhibiting action.

A third object of the present invention is to provide a non-color forming coupling compound which provides not only intralayer effects but also provides sufficient interlayer effects, and, therefore, which provides a satisfactory color correction effect.

A fourth object of the present invention is to provide a non-color forming coupling compound which is stable against ageing, and which does not exhibit a desensitization action.

A fifth object of the present invention is to provide a non-color forming coupling compound which is substantially colorless and which yields, upon reaction with the oxidation product of a developing agent, a substantially colorless product or a colored product which does not substantially contribute to the finished color image or which becomes substantially colorless during the course of photographic treatment.

A sixth object of the present invention is to provide a non-color forming coupling compound which provides reduced mottle due to contamination of a developer solution.

A seventh object of the present invention is to provide a silver halide photographic material containing a novel non-color forming coupling compound.

An eighth object of the present invention is to provide a photographic processing solution containing a novel non-color forming coupling compound.

A ninth object of the present invention is to provide a method for forming an image wherein the processing is carried out in the presence of a novel non-color forming coupling compound.

These objects of the present invention are attained by a compound which, upon reaction with the oxidation product of a color developing agent, simultaneously releases a compound having a development inhibiting action and forms a substantially a colorless compound or a colored compound whose color is changed and such becomes substantially colorless in a developer solution or in another solution used in the photographic treatment subsequent to the development processing, and which is represented by the following general formula (I):

$$R-\underset{\underset{H}{|}}{\overset{\overset{X}{|}}{C}}-Y \qquad (I)$$

wherein

R represents a hydrogen atom; an alkyl group; an aryl group; a halogen atom; an —O—Z group in which Z represents an alkyl group, an aryl group, a heterocyclic group, an acyl group or —SO$_2$R$_2$ in which R$_2$ represents an alkyl group, an aryl group or a heterocyclic group; a 5-membered or 6-membered heterocyclic group; or Y;

X represents

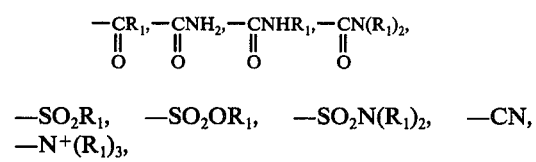

$-SO_2R_1$, $-SO_2OR_1$, $-SO_2N(R_1)_2$, $-CN$, $-N^+(R_1)_3$,

or Y; wherein R$_1$ represents an aliphatic group, an aryl group or a heterocyclic group or two R$_1$ groups may combine and together with the nitrogen atom to which the two R$_1$ groups are attached form a nitrogen-containing heterocyclic group; and Y represents a group which is capable of being released from the compound represented by the general formula (I) upon reaction with the oxidation product of a developing agent to provide a compound which has a development inhibiting effect and which is selected from the group consisting of a benzotriazolyl group, a naphthotriazolyl group and a triazolyl group, and each of which groups may be substituted with one or more substituents, which may be the same or different, selected from the group consisting of a heterocyclic group, an aralkyloxy group, a sulfamoyl group, a ureido group, a sulfonamido group, a group represented by the following general formula (II):

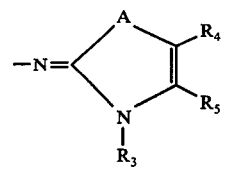

wherein A represents a sulfur atom, a selenium atom or an oxygen atom; R$_3$ represents an aliphatic group; and R$_4$ and R$_5$, which may be the same or different, each represents a hydrogen atom, an aliphatic group, an alkoxy group, a hydroxy group or an aromatic group or R$_4$ and R$_5$ may combine and represent an atomic group necessary to form a benzene ring or a naphthalene ring, and a group represented by the following general formula (III):

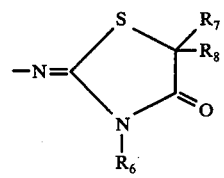

wherein R$_6$ represents an aliphatic group or an aromatic group; and R$_7$ and R$_8$, which may be the same or different, each represents a hydrogen atom, an aliphatic group or an aromatic group.

BRIEF DESCRIPTION OF THE ACCOMPANYING DRAWINGS

FIG. 1 shows a cross sectional view of the layer structure of Samples 401 to 404 prepared in Example 4.

FIG. 2 indicates the definition of $\Delta D^G$ which means the amount of interlayer effects obtained by exposure in the manner as described in Example 4.

DETAILED DESCRIPTION OF THE INVENTION

Figure 1:
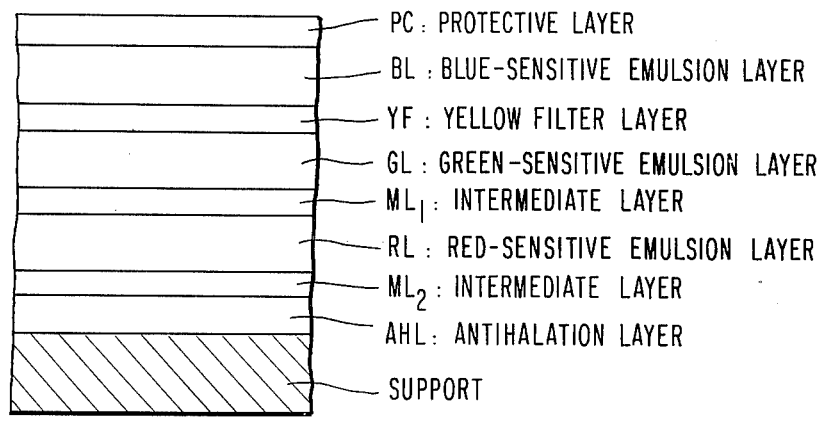

In the general formula (I) above, R represents a hydrogen atom; an alkyl group (preferably, an alkyl group having 1 to 5 carbon atoms such as a methyl group, an ethyl group, a butyl group, etc.); an aryl group (preferably, an aryl group of the phenyl series or the naphthyl series and which can be substituted with one or more substituents, for example, a halogen atom, a hydroxy group, a phenyl group, etc.); a halogen atom (such as a chlorine atom, etc.); an —O—Z group in which Z represents an alkyl group, an aryl group, a heterocyclic group, an acyl group, or an —$SO_2R_2$ group in which $R_2$ represents an alkyl group, an aryl group or a heterocyclic group; a 5-membered or 6-membered heterocyclic group (which contains at least one hetero atom such as a nitrogen atom, an oxygen atom, a sulfur atom or a selenium atom and which has at least one condensed ring such as a benzene ring or a naphthalene ring, for example, a benzoxazole ring, a benzthiazole ring, etc.); or Y.

The alkyl group represented by Z or $R_2$ is preferably an alkyl group having 1 to 18 carbon atoms and can be additionally substituted with one or more of a halogen atom such as a chlorine atom and a bromine atom, a hydroxy group, a phenyl group, etc. Suitable examples of alkyl groups for Z or $R_2$ include a methyl group, an ethyl group, a butyl group, an octyl group, a hexadecyl group, etc.

The aryl group represented by Z or $R_2$ can be a monocyclic or bicyclic aryl group having 6 to 25 carbon atoms, typically a phenyl group or a naphthyl group and these groups can be substituted with one or more of a halogen atom such as a chlorine atom and a bromine atom, a hydroxy group, an alkoxy group having 1 to 20 carbon atoms such as a methoxy group, an ethoxy group, a butoxy group, an octyloxy group, etc., an alkyl group having 1 to 20 carbon atoms such as a methyl group, an ethyl group, a butyl group, an octyl group, a hexadecyl group, etc., and the like.

Suitable examples of aryl groups for Z or $R_2$ are a phenyl group, a p-methoxyphenyl group, a naphthyl group, etc.

The heterocyclic group represented by Z or $R_2$ is preferably a 5-membered or 6-membered heterocyclic group containing one or more hetero atoms such as a nitrogen atom, an oxygen atom and a sulfur atom, e.g., a pyridine group, a furan group, a thiophene group, etc.

These heterocyclic groups can be further substituted with one or more monovalent groups such as an alkyl group, an aryl group, an alkoxy group, an aryloxy group, a hydroxy group, a carboxyl group and a halogen atom.

The acyl group represented by Z is a group represented by the formula

wherein $R_9$ is preferably an alkyl group or an aryl group. The alkyl group or the aryl group represented by $R_9$ is the same as defined above for Z.

As described above, X represents

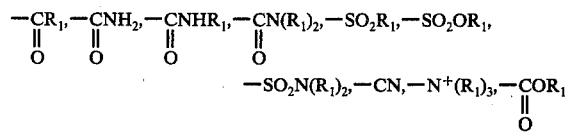

or Y wherein $R_1$ represents a saturated or olefinically unsaturated aliphatic group having 1 to 18 carbon atoms [which can be straight chain, branched chain or cyclic (e.g., a methyl group, an ethyl group, a butyl group, an octyl group, a hexadecyl group, etc.) and which can be substituted additionally with one or more substituents, for example, an alkoxy group (e.g., having 1 to 20 carbon atoms, such as a methoxy group, an isopropoxy group, etc.), a halogen atom (such as a chlorine atom, a bromine atoms, etc.), a hydroxy group, a carboxy group, a sulfo group, a heterocyclic group (e.g., 5-membered or 6-membered heterocyclic group, such as a tetrahydrofuran group, a pyridine group, etc.), an aryl group (e.g., a monocyclic or bicyclic aryl group having 6 to 25 carbon atoms, such as a phenyl group, a tolyl group, etc.), an aralkyl group (e.g., having 7 to 25 carbon atoms, such as a benzyl group, a phenylethyl group, styryl group, etc.), and the like], an aryl group (e.g., a monocyclic or bicyclic aryl group having 6 to 25 carbon atoms [for example, a phenyl group, a naphthyl group, etc.], which can be unsubstituted or substituted with one or more monovalent substituents which may be the same or different, for example, a halogen atom (such as a fluorine atom, a chlorine atom, a bromine atom, etc.), a nitro group, a cyano group, a thiocyano group, a hydroxy group, an alkoxy group (preferably an alkoxy group having 1 to 15 carbon atoms, such as a methoxy group, an isopropoxy group, an octoxy group, etc.), an aryloxy group (e.g., a monocyclic or bicyclic aryloxy group having 6 to phenyl carbon atoms, such as a phenoxy group, a nitrophenoxy group, etc.), an alkyl group (e.g., a straight chain, branched chain or cyclic alkyl group and preferably an alkyl group having 1 to 15 carbon atoms, such as a methyl group, an ethyl group, a dodecyl group, etc.), an alkenyl group (e.g., straight chain, branched chain or cyclic alkenyl group and preferably an alkenyl group having 1 to 15 carbon atoms, such as an allyl group, etc.), an aryl group (preferably an aryl group having 6 to 10 carbon atoms, such as a phenyl group, a tolyl group, etc.), an amino group (for example, an unsubstituted amino group, a straight chain, branched chain or cyclic alkylamino group having 1 to 15 carbon atoms, such as a diethylamino group, an octylamino group, etc.), a carboxy group, an acyl group (e.g., an alkanoyl or aroyl group and preferably an acyl group having 2 to 16 carbon atoms, such as an acetyl group, a decanoyl group, etc.), an alkoxycarbonyl group (preferably an alkoxycarbonyl group having 1 to 20 carbon atoms in the alkyl moiety which can be straight chain, branched chain or cyclic, such as a methoxycarbonyl group, a butoxycarbonyl group, an octoxycarbonyl group, a dodecyloxycarbonyl group, a 2-phenylethyloxy group, a 2-methoxyethoxycarbonyl group, etc.), an aryloxycarbonyl group (preferably an aryloxycarbonyl group having 6 to 20 carbon atoms in the aryl moiety which can be monocyclic or bicyclic, such as a phenoxycarbonyl group, a tolyloxycarbonyl group, etc.), a carbamoyl group (e.g., an alkyl or arylcarbamoyl group, for example, an ethylcarbamoyl, an octylcarbamoyl, etc.), an acylamino group (e.g., an alkanoylamino or aroylamino group and preferably an acylamino group having 2 to 21 carbon atoms, such as an acetamido group, an octanamido group, a 2,4-di-tert-pentylphenoxyacetamido group, etc.), a sulfo group, an alkylsulfonyl group (preferably an alkylsulfonyl group having 1 to 15 carbon atoms in the alkyl moiety which can be straight chain, branched chain or cyclic, such as a methylsulfonyl group, an octylsulfonyl group, etc.), an arylsulfonyl group (e.g., a monocyclic or bicyclic arylsulfonyl group and preferably an arylsulfonyl group having 6 to 20 carbon atoms, such as a phenylsulfonyl group, etc.), an alkoxysulfonyl group (preferably an alkoxysulfonyl group having 1 to 15 carbon atoms in the alkoxy moiety which can be straight chain, branched chain or cyclic, such as a methoxysulfonyl group, an octoxysulfonyl group, etc.), an aryloxysulfonyl group (e.g., a monocyclic or bicyclic aryloxysulfonyl group and preferably an aryloxysulfonyl group having 6 to 20 carbon atoms, such as a phenoxysulfonyl group, etc.), a sulfamoyl group (preferably an alkyl or arylsulfamoyl group having 1 to 15 carbon atoms, such as diethylsulfamoyl group, an octylsulfamoyl group, an N,N-methyloctadecylsulfamoyl group, etc.), a sulfonamido group (preferably an alkyl or arylsulfonamido group having 1 to 15 carbon atoms, such as a methanesulfonamido group, an octanesulfonamido group, etc.), and the like, or a divalent substituent which forms a condensed ring with the phenyl group (for example, a naphthalene ring, etc.), or a heterocyclic group (for example, a 5-membered or 6-membered heterocyclic group containing at least one hetero atom such as a nitrogen atom, an oxygen atom, a sulfur atom or a selenium atom, which group has one or more fused benzene rings or naphthalene rings. When two or more $R_1$ groups are present, the $R_1$ groups can be the same or different. Alternatively, two $R_1$ groups in, for example, an $-N^+(R_1)_3$ group or an $-SO_2N(R_1)_2$ group can combine together with the nitrogen atom and form a 5-membered or 6-membered heterocyclic ring containing one or more additional hetero atoms such as an oxygen atom, a sulfur atom and a nitrogen atom (for example, a piperidine ring, a pyrrolidine ring, a morpholine ring, etc.).

Y represents a benzotriazolyl group, a naphthotriazolyl group, a triazolyl group, and which group can be substituted with one or more substituents, which may be the same or different, selected from a 5-membered or 6-membered heterocyclic group (e.g., containing one or more of hetero atoms such as an oxygen atom, a sulfur atom and a nitrogen atom, for example, a 4-thiazolin-2-thione group, etc.), an aralkyloxy group having 7 to 30 carbon atoms (e.g., in which the aryl moiety thereof can be monocyclic or bicyclic and the alkyl moiety thereof can be straight chain, branched chain or cyclic, for example, a benzyloxy group, a phenethoxy group, etc.), a ureido group, an alkyl- or arylsulfonamido group, an alkyl- or arylsulfamoyl group, a group represented by the following general formula (II):

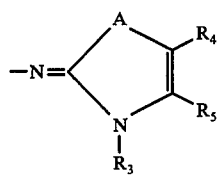

(II)

wherein A represents a sulfur atom, a selenium atom or an oxygen atom; $R_3$ represents an aliphatic group having 1 to 25 carbon atoms (preferably an alkyl group having 1 to 12 carbon atoms); and $R_4$ and $R_5$, which may be the same or different, each represents a hydrogen atom, an aliphatic group having 1 to 25 carbon atoms (preferably an alkyl group having 1 to 12 carbon atoms), an alkoxy group having 1 to 25 carbon atoms, a hydroxy group or an aromatic group having 6 to 30 carbon atoms or $R_4$ and $R_5$ may combine and represent an atomic group necessary to form a benzene ring or a naphthalene ring, and a group represented by the following general formula (III):

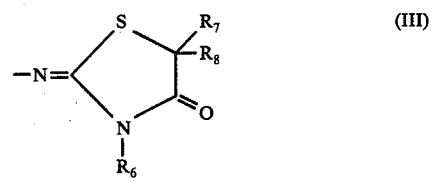

(III)

wherein $R_6$ represents an aliphatic group having 1 to 25 carbon atoms (preferably an alkyl group having 1 to 12 carbon atoms) or an aromatic group having 6 to 30 carbon atoms; and $R_7$ and $R_8$, which may be the same or different, each represents a hydrogen atom, an aliphatic group having 1 to 25 carbon atoms (preferably an alkyl group having 1 to 12 carbon atoms) or an aromatic group having 6 to 30 carbon atoms.

Suitable examples of alkyl groups having 1 to 12 carbon atoms for $R_3$, $R_4$, $R_5$, $R_6$, $R_7$ and $R_8$ include a methyl group, an ethyl group, an n-butyl group, an n-hexyl group, a cyclohexyl group, an n-octyl group, a 2-ethylhexyl group, an n-decyl group, etc., which may be substituted with one or more monovalent groups such as an alkyloxy group, an aryloxy group, an aryl group, a hydroxy group, a carboxyl group and a halogen atom.

Suitable examples of alkoxy groups having 1 to 25 carbon atoms for $R_4$ and $R_5$ include a methoxy group, an ethoxy group, an n-butoxy group, an n-octyloxy group, etc.

Suitable examples of aromatic groups having 6 to 30 carbon atoms for $R_4$, $R_5$, $R_6$, $R_7$ and $R_8$ include a monocyclic aromatic group such as a phenyl group, etc., and a bicyclic aromatic group such as a naphthyl group, etc., and the like. These aromatic groups can be further substituted with one or more monovalent groups such as an alkyl group, an aryl group, an alkoxy group, an aryloxy group and a halogen atom, e.g., a fluorine atom, a chlorine atom, etc.

The benzene or naphthalene ring formed by $R_4$ and $R_5$ can be further substituted with one or more monovalent groups such as an alkyl group, an aryl group, an alkoxy group, an aryloxy group and a halogen atom, e.g., a fluorine atom, a chlorine atom, etc.

Of the compounds represented by the general formula (I), the compounds in which X is

wherein $R_1$ represents a phenyl group which can be substituted with one or more substituents, which may be the same or different, and selected from the substituents described above for the aryl group of $R_1$; and Y is a benzotriazolyl group substituted with one or more benzyloxy groups or thiazolinylidenamino groups represented by the following general formula (IV):

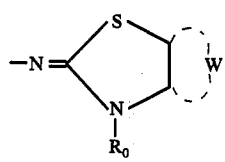
(IV)

wherein W represents a condensed aromatic ring (for example, a benzene ring, etc.) which ring may be substituted with one or more of an alkyl group (e.g., a straight chain, branched chain or cyclic alkyl group having 1 to 20 carbon atoms, for example, a methyl group, an ethyl group, a propyl group, etc.), an alkoxy group (e.g., a straight chain, branched chain or cyclic alkoxy group having 1 to 20 carbon atoms, for example, a methoxy group, an ethoxy group, etc.), a halogen atom (for example, a chlorine atom, a bromine atom, etc.) and the like; and $R_O$ represents an aliphatic group (e.g., having 1 to 20 carbon atoms, for example, a straight chain, branched chain or cyclic alkyl group having 1 to 4 carbon atoms, a straight chain, branched chain or cyclic alkyl group substituted with one or more of a straight chain, branched chain or cyclic alkoxy group having 1 to 20 carbon atoms, a halogen atom such as a chlorine atom, and a bromine atom, a monocyclic or bicyclic aryl group, etc.) or a monocyclic or bicyclic aryl group having 6 to 25 carbon atoms [for example, a 5- or 6-benzyloxybenzotriazolyl group, a 5- or 6-(3-methylbenzothiazolinyliden)aminobenzotriazolyl group, a 5- or 6-(3-ethylbenzothiazolinyliden)aminobenzotriazolyl group, a 5- or 6-(3-benzylbenzothiazolinyliden)aminobenzotriazolyl group, a quinoxalino[2,3-f]benzotriazolyl group, etc.], or a 1,2,4-triazolyl group substituted with the above-described thiazolinylidene group [for example, a 3,5-di-(3-methylbenzothiazolinyliden)amino-1,2,4-triazolyl group, etc.] are particularly preferred. Among the non-color forming coupling compounds described above, compounds in which a benzotriazolyl group, a naphthotriazolyl group or a triazolyl group represented by Y is bonded to the coupling position through the nitrogen atom at the 1-position of the triazole ring are particularly preferred.

The non-color forming coupling compounds of the present invention have remarkably superior properties in comparison with known non-color forming coupling compounds in that they have a high coupling reactivity and an extremely high development inhibiting effect, reduced graininess and improved sharpness, and that the compounds per se are stable and thus the light-sensitive materials containing the compounds have improved ageing properties.

Typical examples of the compounds represented by the general formula (I) are illustrated in the following, but the present invention should not be construed as being limited to these compounds.

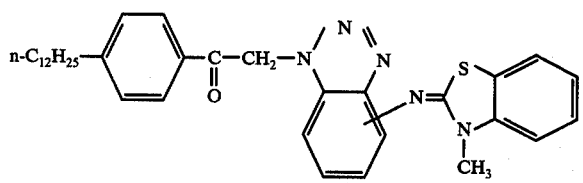
(1)

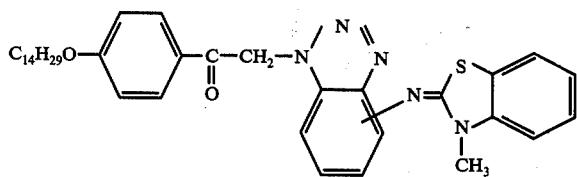
(2)

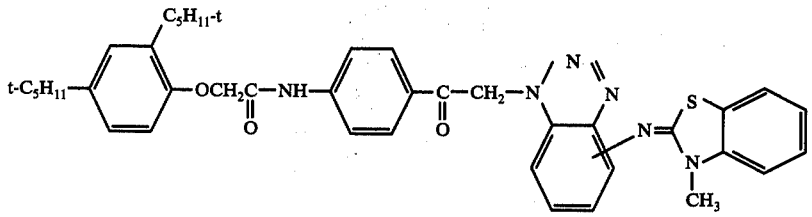
(3)

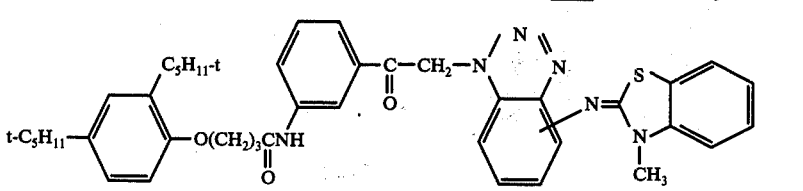
(4)

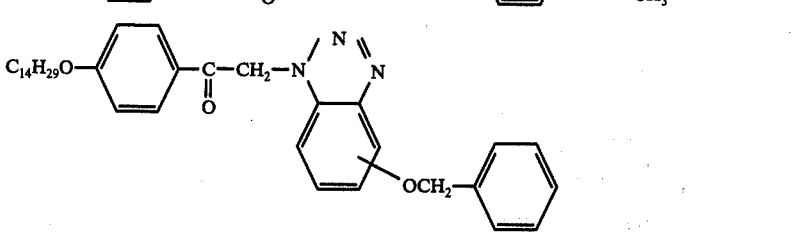
(5)

-continued
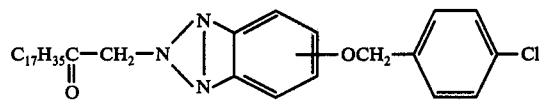 (6)
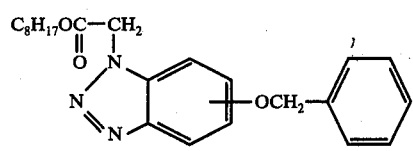 (7)
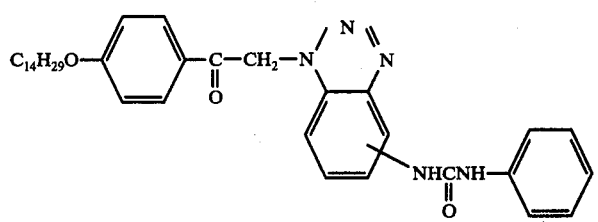 (8)
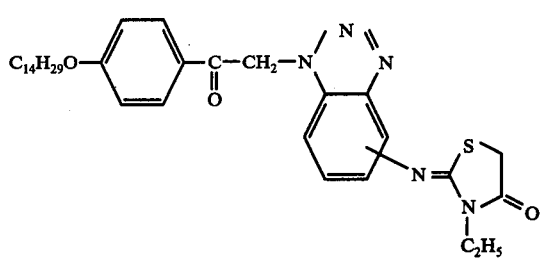 (9)
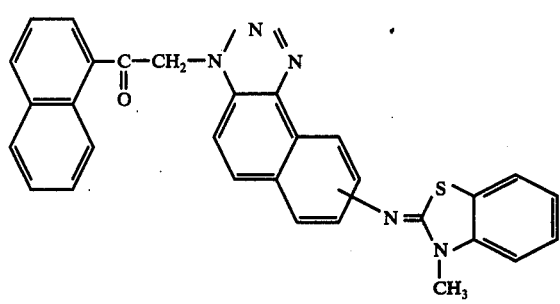 (10)
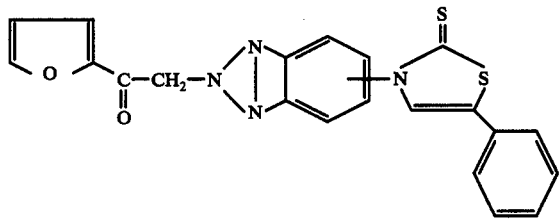 (11)
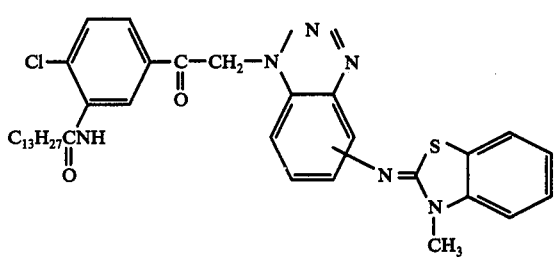 (12)
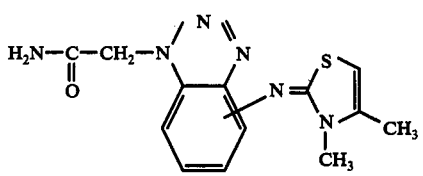 (13)

-continued
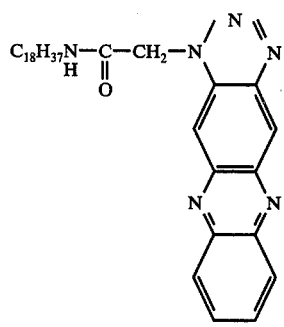
(14)
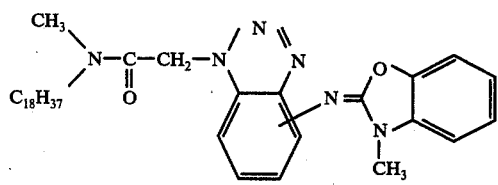
(15)
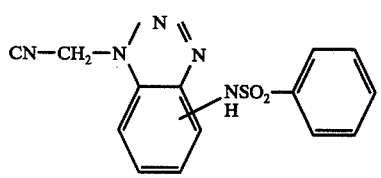
(16)
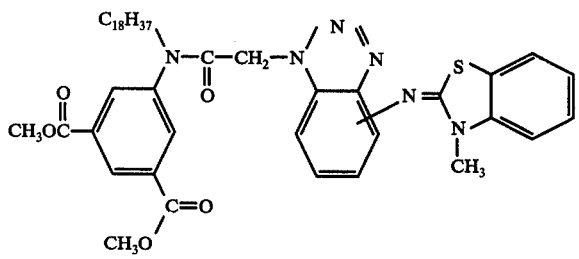
(17)
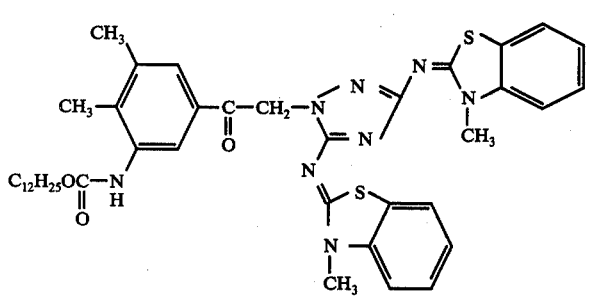
(18)
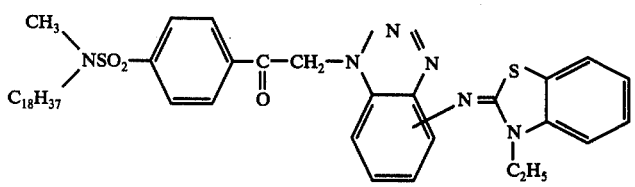
(19)
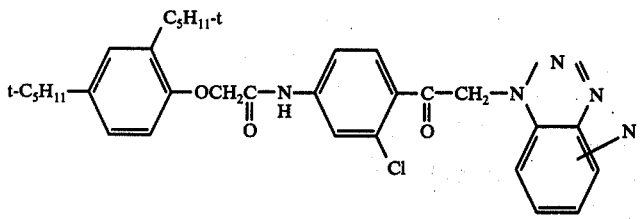
(20)

-continued
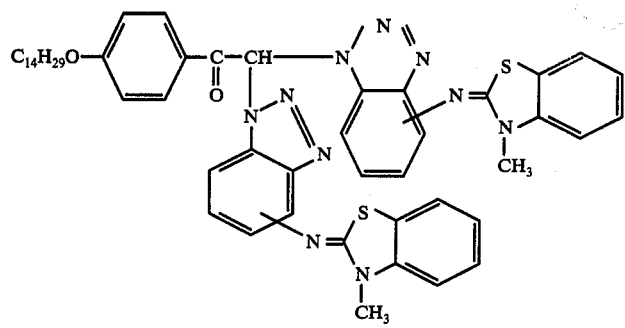
(21)
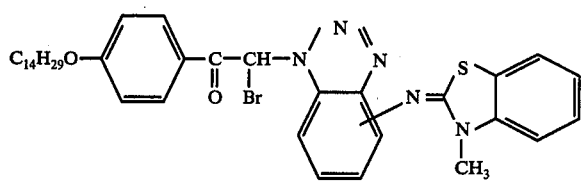
(22)
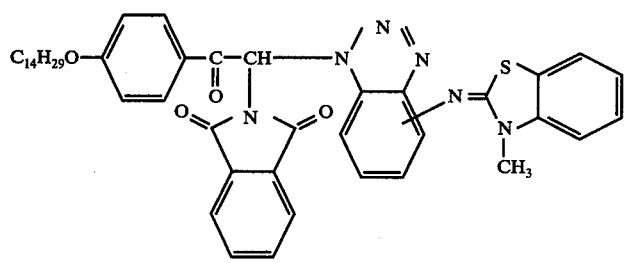
(23)
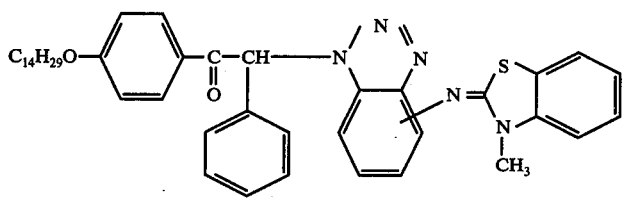
(24)
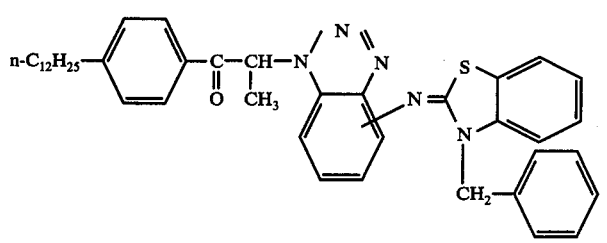
(25)
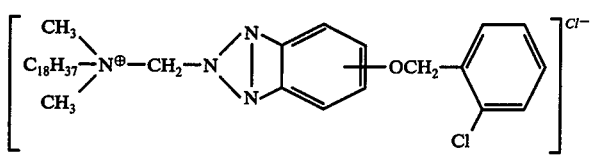
(26)
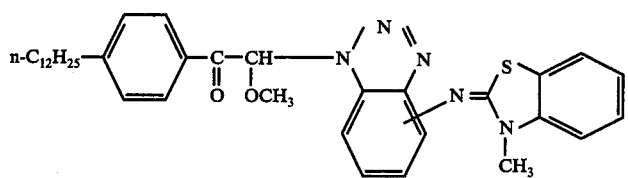
(27)
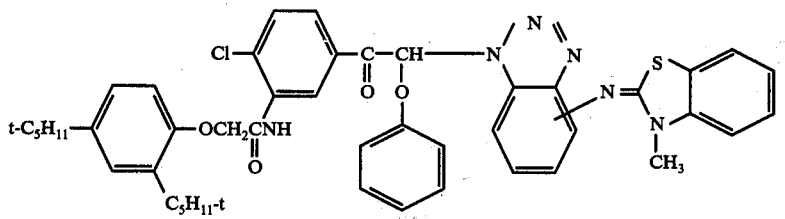
(28)

-continued

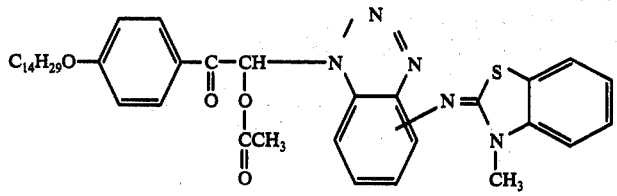
(29)

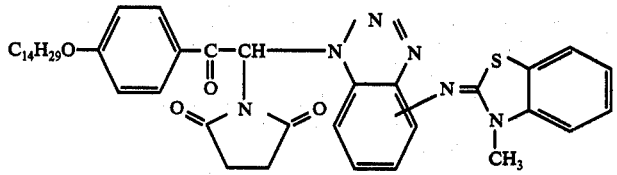
(30)

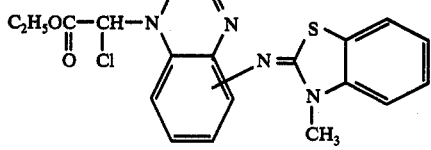
(31)

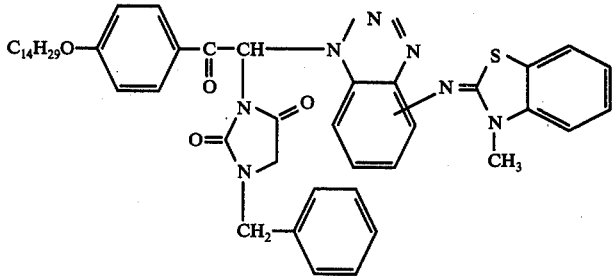
(32)

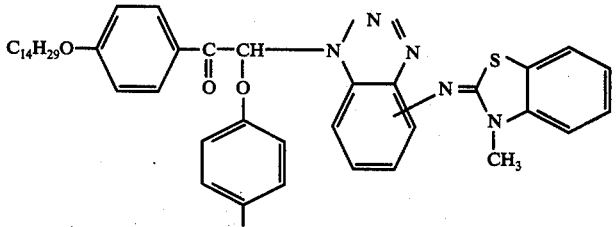
(33)

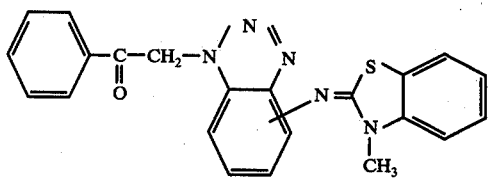
(34)

The compounds represented by the general formula (I) can be prepared by reacting a compound represented by the general formula (I')

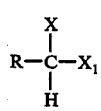  (I')

wherein R and X are the same as defined in the general formula (I) and $X_1$ represents a halogen atom, preferably a chlorine atom or a bromine atom, with a triazole derivative employing the method used for the preparation of the two equivalent yellow-dye forming coupl described in U.S. Pat. No. 4,022,620. Synthesis examples of the compound represented by the general formula (I') are described in U.S. Pat. No. 3,928,041, and methods for the preparation of the triazole derivatives which can be used in this invention are described in U.S. patent application Ser. No. 678,816 filed Apr. 21, 1976, corresponding to German Patent Application (OLS) No. 2,617,345.

Typical methods for preparation of the compounds represented by the general formula (I) are illustrated below. Other compounds can also be prepared in a manner similar to these methods. Unless otherwise indicated herein, all parts, percents, ratios and the like are by weight.

SYNTHESIS EXAMPLE 1

Preparation of Compound (1)

32.0 g (0.1 mol) of p-n-dodecyl-ω-chloroacetophenone and 42.2 g (0.15 mol) of 5-(3-methyl-2-benzothiazolinyliden)aminobenzotriazole were dissolved in 160 ml of dimethylformamide and to the solution 20.0 g (0.2 mol) of triethylamine was added dropwise at room temperature (about 20° – 30° C) with stirring. After stirring the mixture for about 5 hours, 400 ml of water and 200 ml of chloroform were added to the reaction mixture and while stirring 20 ml of concentrated hydrochloric acid (36%) was added dropwise thereto at room temperature. The solid deposited was removed by filtration and the filtrate was washed with 300 ml of 2N hydrochloric acid and then washed twice with 200 ml of water and dried with anhydrous sodium sulfate. The solvent was removed under reduced pressure to obtain the desired compound which was recrystallized from ethanol to yield 54.0 g (0.095 mol). Yield: 95.0%, M.P.: 97 to 99° C.

SYNTHESIS EXAMPLE 2

Preparation of Compound (2)

27.0 g (0.07 mol) of p-n-tetradecyloxy-ω-chloroacetophenone and 28.0 g (0.1 mol) of 5-(3-methyl-2-benzothiazolinyliden)aminobenzotriazole were dissolved in 150 ml of dimethylformamide and to the solution 14.0 g (0.14 mol) of triethylamine was added dropwise at room temperature with stirring. In the same manner as described in Synthesis Example 1, Compound (2) was obtained which was recrystallized from ethanol to yield 36.4 g (0.064 mol). Yield: 91.5%, M.P.: 102° to 104° C.

SYNTHESIS EXAMPLE 3

Preparation of Compound (23)

37.0 g (0.1 mol) of p-n-tetradecyloxy-ω-chloroacetophenone and 18.5 g (0.1 mol) of the potassium salt of phthalimide were dissolved in 200 ml of dimethylformamide. After stirring the mixture for 10 hours at room temperature, the reaction solution was poured into 2.0 liters of water and the crystals deposited were collected and recrystallized from ethanol to prepare p-n-tetradecyloxy-ω-phthalimidacetophenone. 30 g (0.07 mol) of p-n-tetradecyloxy-ω-phthalimidacetophenone was dissolved in 130 ml of chloroform and to which 11.2 g (0.07 mol) of bromine dissolved in 30 ml of chloroform was added dropwise over a period of about 1 hour while refluxing the mixture by heating. The reaction solution was washed twice with 200 ml of water and dried with anhydrous sodium sulfate. The solvent was removed under reduced pressure and the oily product residue was recrystallized from n-hexane to obtain 30.0 g of p-n-tetradecyloxy-ω-bromo-ω-phthalimidacetophenone. 20.3 g (0.04 mol) of p-n-tetradecyloxy-ω-bromo-ω-phthalimidacetophenone and 16.9 g (0.06 mol) of 5-(3-methyl-2-benzothiazolinyliden)aminobenzotriazole were dissolved in 100 ml of dimethylformamide and to the solution 8.0 g (0.08 mol) of triethylamine was added dropwise at room temperature with stirring. In the same manner as described in Synthesis Example 1, Compound (23) was obtained which was recrystallized from acetonitrile to yield 28.1 g. Yield: 93%, M.P.: 153° to 155° C.

The non-color forming coupling compounds of the present invention can be incorporated into a photographic emulsion layer using known dispersion methods. For example, the method described hereinafter can be used.

The non-color forming coupling compound of the present invention can be advantageously mixed with a solvent dispersion by dissolving the coupling compound into either a water-immiscible organic solvent having a high boiling point (higher than about 170° C), an organic solvent having a low boiling point or a water-soluble organic solvent, or into a mixture of such a water-immiscible organic solvent with a high boiling point and/or such an organic solvent with a low boiling point and/or such a water-soluble organic solvent.

All water-immiscible organic solvents having high boiling points as disclosed in U.S. Pat. No. 2,322,027 can be employed as solvents for the above-described purpose. Preferred examples of such solvents include di-n-butyl-phthalate, benzylphthalate, triphenyl phosphate, tri-o-cresyl phosphate, diphenyl-mono-p-tert-butylphenyl phosphate, dioctyl phthalate, dibutyl sebacate, acetyl tributyl citrate, tri-tert-octyltrimellitate, n-nonylphenol, dioctylbutyl phosphate, N,N-diethyllaurylamide, 3-pentadecylphenyl ethyl ether, 2,5-di-sec-amylphenyl butyl ether, and the like.

Organic solvents having a low boiling point (lower than about 170° C) or water-soluble organic solvents which can be employed together with or instead of the above-described solvents having a high boiling point are described in U.S. Pat. Nos. 2,801,171, 2,801,170, 2,949,360 and the like.

In order to disperse the non-color forming coupling compounds of the present invention, a homogenizer for emulsification, a colloid mill, an ultrasonic emulsifying apparatus and the like can be usefully employed.

The non-color forming compounds of the present invention may be used individually or as a combination of two or more thereof, or can be employed together with known two equivalent and/or four equivalent couplers. Moreover, the coupling compounds of the present invention can also be used in combination with colored couplers instead of DIR couplers as disclosed in U.S. Pat. No. 3,703,375. These couplers may be mixed in the same dispersed droplet or each of these couplers can be dispersed separately.

The amount of the non-color forming coupling compound employed in the practice of the present invention can be varied over a wide range depending on the type of light-sensitive material or processing used. In the case of incorporation of the coupler in a light-sensitive material, the coupling compound can be effectively employed in an amount of particularly from about 0.0005 to about 0.5 per mol of the silver halide present in the emulsion. On the other hand, in the case of addition of the coupler to a developer solution, the coupling compound may be effectively employed in an amount of particularly from about $1 \times 10^4$ mol to about $1 \times 10^{-1}$ mol per 1,000 ml of the developer solution.

The non-color forming coupling compound of the present invention can be used in multilayer color light-sensitive materials having a superposed layer structure as disclosed in U.S. Pat. No. 3,726,681, British Pat. Nos. 818,687 and 923,045, U.S. Pat. No. 3,516,831, Japanese Patent Application No. 5,179/75, etc. Further, the coupling compound of the present invention can be used together with or instead of DIR couplers according to the method disclosed in German Patent Application (OLS) No. 2,322,165.

The silver halide photographic emulsions which can be used in the practice of the present invention are dispersions prepared by dispersing a light-sensitive silver halide such as silver chloride, silver bromide, silver chlorobromide, silver chloroiodide, silver iodobromide, silver chloroiodobromide or the like into a hydrophilic polymer such as gelatin as colloidal particles using any conventional methods. The silver halide photographic emulsions which can be employed in the practice of the present invention can contain a wide variety of conventional additives for silver halide color photographic emulsions, for example, various chemical sensitizers, stabilizers, anti-fogging agents, hardening agents, spectral sensitizers, surface active agents and the like. The photographic emulsions can be coated on an appropriate support in a conventional manner.

The light-sensitive materials containing the non-color forming coupling compounds of the present invention can be subjected to a color development using an aromatic primary amine compound such as a p-phenylenediamine derivative, as well as to a black-and-white development using a developer solution containing a known black-and-white developing agent.

The non-color forming coupling compounds of the present invention can also be used by adding them to either a color developer solution or a black-and-white developer solution.

The non-color forming coupling compounds of the present invention can be used for various kinds of silver halide photographic light-sensitive materials, for example, they are useful for both black-and-white and color light-sensitive materials. Moreover, the coupling compounds can be applied to silver halide photographic light-sensitive materials used for various purposes such as black-and-white light-sensitive materials for general use, black-and-white light-sensitive materials for printing, light-sensitive materials for X-ray or electron beam recording, black-and-white light-sensitive materials having a high resolving power, color light-sensitive materials for general use, color light-sensitive materials of the direct positive type, color light-sensitive materials for X-ray photography, color light-sensitive materials of the diffusion transfer type, color light-sensitive materials having a low silver content to which a color intensifying technique is employed and the like.

Since the non-color forming coupling compounds of the present invention are very reactive, they react rapidly with the oxidation product of a color developing agent to produce not only substantially colorless coupling products but also release development inhibitors. Therefore, only a small amount of the coupling compounds provides an excellent DIR effect (an imagewise development inhibiting effect as described hereinbefore) and provides control of image tone, an image of a reduced graininess, and an image of increased sharpness, an improvement in color reproduction, and, further, prevents the quality of the image from deteriorating upon storage.

The present invention will be further illustrated by reference to the following examples, but the present invention should not be construed as being limiting to the following examples.

EXAMPLE 1

Sample 101

On a transparent cellulose triacetate film support were coated the following First Layer to Fourth Layer in this order and dried to prepare a sample. The composition and method of preparation of the coating solution used for each layer was as follows.

First Layer: Red-Sensitive Emulsion Layer 1 kg of a high speed silver iodobromide emulsion (silver content: 0.6 mol, iodide content: 6 mol%) was spectrally sensitized using $4 \times 10^{-5}$ mol of Sensitizing Dye I and $1 \times 10^{-5}$ of Sensitizing Dye II per mol of silver, respectively. 550 g of Dispersion I prepared by dissolving 100 g of Coupler A into 100 cc of tricresyl phosphate and 200 cc of ethyl acetate, and then dispersing the resulting solution into 1 kg of a 10% aqueous gelatin solution using 4 g of sodium nonylbenzenesulfonate (surface active agent) was added to the spectrally sensitized silver iodobromide emulsion and the mixture was stirred. To the mixture an aqueous solution of 2 g of sodium 2,4-dichloro-6-hydroxytriazine was added as a hardener. The thus-prepared coating solution was coated on a transparent cellulose triacetate film support in a silver coated amount of 2.0 g/m$^2$.

Second Layer: Intermediate Layer 50 g of 2,5-di-tert-octylhydroquinone was dissolved in 100 cc of tricresyl phosphate and dispersed in 1 kg of a 10% aqueous gelatin solution in the same manner as described for Dispersion I. 250 g of the thus prepared dispersion and an aqueous solution of 2 g of sodium 2,4-dichloro-6-hydroxytriazine were added to 1 kg of a 10% aqueous gelatin solution and the mixture stirred. The coating solution was coated in a dry thickness of 1.5 microns.

Third Layer: Green-Sensitive Emulsion Layer 1 kg of a high speed silver iodobromide emulsion (same as used in the First Layer) was spectrally sensitized using $3 \times 10^{-5}$ mol of Sensitizing Dye III and $1 \times 10^{-5}$ mol of Sensitizing Dye IV per mol of silver, respectively. Using 100 g of Coupler B, Dispersion II was prepared in the same manner as described for Dispersion I. 700 g of Dispersion II was added to the spectrally sensitized silver iodobromide emulsion and an aqueous solution of 2 g of sodium 2,4-dichloro-6-hydroxytriazine was added thereto with stirring. The coating solution was coated in a silver coated amount of 1.5 g/m$^2$.

Fourth Layer: Protective Layer

To 1 kg of a 10% aqueous gelatin solution was added 2 g of sodium 2,4-dichloro-6-hydroxytriazine. The solution was coated in a dry thickness of 1.5 microns.

Samples 102 to 105:

Samples 102 to 105 were prepared in the same manner as described for Sample 101 except that the optimum amount of non-color forming coupling compound (as shown in Table 1 below) was additionally incorporated into the coupler solvent in Dispersion II used in the third layer of Sample 101.

The compounds used for the preparation of the above-described samples were:

Sensitizing Dye I: Pyridinium salt of anhydro-5,5'-dichloro-3,3'-disulfopropyl-9-ethylthiacarbocyanine hydroxide Sensitizing Dye II: Triethylamine salt of anhydro-9-ethyl-3,3'-di-(3-sulfopropyl)-4,5,4',5'-dibenzothiacarbocyanine hydroxide Sensitizing Dye III: Sodium salt of anhydro-9-ethyl-5,5'-dichloro-3,3'-disulfopropyloxacarbocyanine Sensitizing Dye IV: Sodium salt of anhydro-5,6,5',6'-tetrachloro-1,1'-diethyl-3,3'-disulfopropoxyethoxyethylimidazolocarbocyanine hydroxide Coupler A: 1-Hydroxy-N-[γ-(2,4-di-tert-amylphenoxy)-propyl]-2-naphthamide Coupler B: 1-(2,4,6-Trichlorophenyl)-3-[3-(2,4-di-tert-amylphenoxyacetamido)benzamido]-5-pyrazolone (4-equivalent coupler)

Non-Color Forming Coupling Compound: p-n-Tetradecyloxy-ω-(1-phenyl-5-tetrazolylthio)acetophenone Samples 101 to 105 were exposed (20 CMS) stepwise using green light and then exposed (20 CMS) uniformly using red light, and subjected to the following processing steps at 38° C. In addition, these samples were line image exposed to soft X-rays through a slit with a 4 mm width and a slit with a 10 μm width and subjected to the same processing as above.

| 1. | Color Development | 3 min 15 sec |
|---|---|---|
| 2. | Bleaching | 6 min 30 sec |
| 3. | Washing | 3 min 15 sec |
| 4. | Fixing | 6 min 30 sec |
| 5. | Washing | 3 min 15 sec |
| 6. | Stabilizing | 3 min 15 sec |

The processing solutions used in the above steps had the following compositions:

| Color Developer Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)-2-methylaniline Sulfate | 4.5 g |
| Water to make | 1 l |
| Bleaching Solution | |
| Ammonium Bromide | 160.0 g |
| Ammonia (28% aq. soln.) | 25.0 ml |
| Sodium Ferric Ethylenediaminetetraacetate | 130 g |
| Glacial Acetic Acid | 14 ml |
| Water to make | 1 l |
| Fixing Solution | |
| Sodium Tetrapolyphosphate | 2.0 g |
| Sodium Sulfite | 4.0 g |
| Ammonium Thiosulfate (70% aq. soln.) | 175.0 ml |
| Sodium Bisulfite | 4.6 g |
| Water to make | 1 l |
| Stabilizing Solution | |
| Formaldehyde (38% aq. soln.) | 8.0 ml |
| Water to make | 1 l |

In the characteristic curve thus obtained, when the gradation of the curve of the red filter optical density vs. log (exposure amount) (which corresponds to the First Layer) is designated $\gamma_R$ and the gradation of the curve of the green filter optical density vs. log (exposure amount) (which corresponds to the Third Layer) is designated $\gamma_G$, the value of $\gamma_R/\gamma_G$ is considered to be the amount of interlayer effects from the Third Layer to the First Layer ($\gamma_G$ values of the samples other than Sample 101 are substantially constant). That is, the value of $\gamma_R/\gamma_G$ is minus and larger numerical values mean larger interlayer effects. The $\gamma_R/\gamma_G$ value of each sample is shown in Table 1 below.

Another set of Samples 101 to 105 was line image exposed to soft X-rays through a slit with a 4 mm width and a slit with a 10 mμ width and subjected to the same processing as described above. The optical density of each sample obtained was measured by microdensitometer tracing with green light. When the density of the line image with a 10 μ width is designated $D_1^G$ and the density of the line image with a 4 mm width is designated $D_2^G$, the value of $(D_1^G - D_2^G)/D_1^G$ means the amount of edge effects of the sample when the sample is observed with green light. That is, a larger value of $(D_1^G - D_2^G)/D_1^G$ means larger edge effects when observed with green light. The value of $(D_1^G - D_2^G)/D_1^G$ of each sample is shown in Table 1 below.

Furthermore, each sample was exposed (20 CMS) stepwise with white light and processed in the same manner as described above and then the graininess of the color image thereof was measured using the conventional RMS (Root Mean Square) method using green light. The results of the RMS graininess at densities of 0.5 and 1.5 are shown in Table 1 below.

TABLE 1

| Sample No. | Non-Color Forming Coupling Compound | | $\gamma_G$ | Inter-image Effects ($\gamma_R/\gamma_G$) | Edge Effects $(D_1^G - D_2^G)/D_1^G$ | RMS Graininess | |
|---|---|---|---|---|---|---|---|
| | Compound | Amount (mol%) | | | | $D_G=0.5$ | $D_G=1.5$ |
| 101* | — | — | 1.40 | 0.05 | 0.04 | 0.055 | 0.078 |
| 102** | Compound (8) | 16 | 0.75 | −0.32 | 0.26 | 0.043 | 0.054 |
| 103** | Compound (5) | 15 | 0.77 | −0.30 | 0.27 | 0.041 | 0.052 |
| 104** | Compound (2) | 13 | 0.77 | −0.35 | 0.30 | 0.038 | 0.049 |
| 105*** | Compound D-1 | 35 | 0.75 | −0.10 | 0.11 | 0.048 | 0.065 |

*Control
**Present invention
***Comparison
Amount: mol% to Coupler B.
RMS Graininess: measured with a slit of 10 μ × 10 μ.
The smaller the numerical value in Table 1 the better the graininess.

From the results shown above it is apparent that Compounds (8), (5) and (2) of the present invention provide larger interlayer effects, edge effects and effects of reducing the graininess of the color image in comparison with the Comparison DIR Coupler D-1 even though the amount of the former is smaller than the latter. It can also be seen that of these compounds Compound (2) exhibits extremely large effects.

EXAMPLE 2

Samples 201 to 204

Samples 201 to 204 were prepared in the same manner as Sample 105 of Example 1 except that Compound (22) of the present invention and Comparison Non-Color Forming Coupling Compounds D-2, D-3 and D-4 were used in the amount shown in Table 2, respectively, in place of Non-Color Forming Coupling Compound D-1 added to the Third Layer of Sample 105.

Samples 102 to 105 prepared as described in Example 1 were also used in this example.

The compounds used for the preparation of the above described samples were:

Comparison Non-Color Forming Coupling Compound D-2 p-Tetradecyloxy-ω-bromo-ω-(1-phenyl-5-tetrazolylthio)acetophenone

Comparison Non-Color Forming Coupling Compound D-3 p-Tetradecyloxy-ω-di-(1-phenyl-5-tetrazolylthio)acetophenone

Comparison Non-Color Forming Coupling Compound D-4 p-Tetradecyloxy-ω-(4-methoxyphenoxy)-ω-(1-phenyl-5-tetrazolylthio)acetophenone

These samples were stored for 4 days either under room temperature conditions (20° C, 70% RH) or under conditions of high humidity and high temperature (40° C, 80% RH), and then they were exposed (20 CMS) stepwise using white light and processed in the same manner as described in Example 1. The optical densities with green light and red light of the thus-processed samples were measured and the characteristic values obtained are shown in Table 2.

TABLE 2

| Sample No. | Non-Color Forming Coupling Compound | | Storage at Room Temperature | | | | Storage at 40° C, 80% RH | | | |
|---|---|---|---|---|---|---|---|---|---|---|
| | | | Relative Sensitivity | | Gamma | | Relative Sensitivity | | Gamma | |
| | Compound | Amount (mol%) | Green Light | Red Light | Green Light | Red Light | Green Light | Red Light | Green Light | Red Light |
| 102** | Compound (8) | 16 | 100 | 100 | 0.78 | 1.15 | 99 | 98 | 0.77 | 0.16 |
| 103** | Compound (5) | 15 | 99 | 99 | 0.80 | 1.13 | 99 | 97 | 0.78 | 1.12 |
| 104** | Compound (2) | 13 | 98 | 100 | 0.80 | 1.09 | 96 | 100 | 0.80 | 1.05 |
| 201** | Compound (22) | 15 | 99 | 98 | 0.81 | 1.10 | 97 | 96 | 0.80 | 1.13 |
| 105*** | Compound D-1 | 35 | 98 | 100 | 0.78 | 1.35 | 80 | 92 | 0.69 | 1.03 |
| 202*** | Compound D-2 | 35 | 97 | 99 | 0.81 | 1.33 | 79 | 89 | 0.66 | 0.98 |
| 203*** | Compound D-3 | 35 | 99 | 98 | 0.83 | 1.31 | 65 | 83 | 0.59 | 0.83 |
| 204*** | Compound D-4 | 25 | 97 | 98 | 0.85 | 1.33 | 85 | 93 | 0.70 | 1.10 |

**Present invention
***Comparison
Amount: mol% to Coupler B

From the results described above, it is apparent that Compounds (8), (5), (2) and (22) of the present invention act to reduce the sensitivity and gamma of the layer to which the compounds are added or the emulsion layer adjacent thereto to an extremely lesser extent in comparison with Comparison Non-Color Forming Coupling Compounds D-1, D-2, D-3 and D-4 under storage at high humidity and high temperature. This illustrates that the compounds of the present invention are extremely stable in comparison with the above-described comparison non-color forming coupling compounds.

Further, the gamma value measured with red light in the sample containing the compound of the present invention stored at room temperature is smaller than that of the sample containing the comparison non-color forming coupling compound. This illustrates that the interlayer effect from the green-sensitive layer to the red-sensitive layer of the compound of the present invention is larger than that of the comparison non-color forming coupling compound.

EXAMPLE 3

On a cellulose triacetate film support were coated layers having the compositions set forth below to prepare a multilayer color light-sensitive material. The compounds indicated by an asterisk are the same compounds as described in Example 1.

First Layer: Antihalation Layer (AHL)

A gelatin layer containing 300 mg/m² of black colloidal silver

Second Layer: Intermediate Layer (ML)

A gelatin layer containing a dispersion of 2,5-di-tert-octylhydroquinone

Third Layer: First Red-Sensitive Emulsion Layer (RL₁)
A silver iodobromide emulsion (iodide content: 5 mol%)
silver coated amount: 1.79 g/m²
Sensitizing Dye I*         6 × 10⁻⁵ mol per mol of silver
Sensitizing Dye II*        1.5 × 10⁻⁵ mol per mol of silver
Coupler A*                 0.04 mol per mol of silver
Coupler C-1                0.0015 mol per mol of silver
Coupler C-2                0.0015 mol per mol of silver
Compound (23)              0.003 mol per mol of silver Fourth Layer: Second Red-Sensitive Emulsion Layer (RL₂)
A silver iodobromide emulsion (iodide content: 4 mol%)
silver coated amount: 1.4 g/m²
Sensitizing Dye I*         3 × 10⁻⁵ mol per mol of silver
Sensitizing Dye II*        1.2 × 10⁻⁵ mol per mol of silver
Coupler A*                 0.005 mol per mol of silver
Coupler C-1                0.0008 mol per mol of silver
Coupler C-2                0.0008 mol per mol of silver
Coupler C-3                0.015 mol per mol of silver
Compound (23)              0.0003 mol per mol of silver Fifth Layer: Intermediate Layer (ML)

Same as the Second Layer

Sixth Layer: First Green-Sensitive Emulsion Layer (GL₁)
A silver iodobromide emulsion (iodide content: 4 mol%)
silver coated amount: 1.5 g/m²
Sensitizing Dye III*       3 × 10⁻⁵ mol per mol of silver
Sensitizing Dye IV*        1 × 10⁻⁵ mol per mol of silver
Coupler B*                 0.05 mol per mol of silver
Coupler M-1                0.008 mol per mol of silver
Compound (23)              0.005 mol per mol of silver Seventh Layer: Second Green-Sensitive Emulsion Layer (GL₂)
A silver iodobromide emulsion (iodide content: 5 mol%)
silver coated amount: 1.6 g/m²
Sensitizing Dye III*       2.5 × 10⁻⁵ mol per mol of silver
Sensitizing Dye IV*        0.8 × 10⁻⁵ mol per mol of silver
Coupler B*                 0.02 mol per mol of silver
Coupler M-1                0.003 mol per mol of silver
Compound (23)              0.001 mol per mol of silver

Eighth Layer: Yellow Filter Layer (YEL)

A gelatin layer containing 300 mg/m² of yellow colloidal silver and a dispersion of 2,5-di-tert-octylhydroquinone

---

Ninth Layer: First Blue-Sensitive Emulsion Layer (BL₁)
A silver iodobromide emulsion (iodide content: 6 mol%)
silver coated amount: 1.5 g/m²
Coupler Y-1           0.25 mol per mol of silver
Compound (23)         0.003 mol per mol of silver
Tenth Layer: Second Blue-Sensitive Emulsion Layer (BL₂)
A silver iodobromide emulsion (iodide content: 6 mol%)
silver coated amount: 1.1 g/m²
Coupler Y-1           0.06 mol per mol of silver

---

Eleventh Layer: Protective Layer (PL)

A gelatin layer containing an ultra-fine grain silver iodobromide emulsion (containing 0.06 mol of silver per kg of emulsion, having an iodide content of 1.4 mol%, and having an average grain size of 0.03 $\mu$), and polymethyl methacrylate particles (having a diameter of about 1.5 $\mu$)
silver coated amount: 2.3 g/m²

A gelatin hardener and a surface active agent as described in Example 1 were incorporated into each of the layers in addition to the above-described components in the same amount as in Example 1 based on the gelatin.

The thus-prepared sample was designated Sample 301.

Samples 302 to 304

Samples 302 to 304 were prepared in the same manner as Sample 301 except that Compound (26), Comparison Non-Color Forming Coupling Compound D-5 and Comparison Non-Color Forming Coupling Compound D-6 were used in place of Compound (23) of Sample 301, respectively. The amount of the Non-Color Forming Coupling Compounds used are shown in Table 3.

TABLE 3

| Layer Added | Sample 301 Compound | Amount | Sample 302 Compound | Amount | Sample 303 Compound | Amount | Sample 304 Compound | Amount |
|---|---|---|---|---|---|---|---|---|
| RL₁ | Compound (23) | 0.003 | Compound (26) | 0.004 | Compound D-5 | 0.006 | Compound D-6 | 0.008 |
| RL₂ | " | 0.003 | " | 0.0004 | " | 0.006 | " | 0.0008 |
| GL₁ | " | 0.005 | " | 0.007 | " | 0.008 | " | 0.015 |
| GL₂ | " | 0.001 | " | 0.0015 | " | 0.002 | " | 0.0025 |
| BL₁ | " | 0.002 | " | 0.004 | " | 0.003 | " | 0.007 |

Amount: mol per mol of silver

The couplers used for the preparation of these samples were as follows.

Coupler C-1: 1-Hydroxy-4-[2-(2-hexyldecyloxycarbonyl)-phenylazo]-2-[N-(1-naphthyl)]naphthamide
Coupler C-2: 1-Hydroxy-4-[4-(ethoxycarbonyl)-phenylazo]-2-(N-dodecyl)naphthamide
Coupler C-3: 1-Hydroxy-4-iodo-2(N-dodecyl)naphthamide
Coupler M-1: 1-(2,4,6-Trichlorophenyl)-3-hexadecanamido-4-(4-hydroxyphenyl)azo-5-pyrazolone
Coupler Y-1: α-(2,4-Dioxo-5,5-dimethyloxazolidinyl)-α-pivaloyl-2-chloro-5-[α-(2,4-di-tert-amylphenoxy)-butyramido]acetanilide
Non-Color Forming Coupling Compound D-5: n-Dodecylsulfonamido-ω-(4-methoxybenzoyloxy)-ω-(1-phenyl-5-tetrazolyl-thio)acetophenone
Non-Color Forming Coupling Compound D-6: p-(β-Carboxy-n-nonadecanamido)-ω-(1-phenyl-5-tetrazolylthio)-acetophenone The samples thus-prepared were exposed (20 CMS) stepwise with white light and subjected to sensitometry as described in Example 1. The sensitivity and gradation in each emulsion layer of Samples 301 to 304 were approximately equal.

Evaluations of the edge effects and the interlayer effects of these samples were carried out in the same manner as described in Example 1. The results obtained are shown in Table 4.

Further, each sample which was fully exposed (20 CMS) to white light was processed in the same manner as described in Example 1. The residual silver present in each sample was determined by fluorescent X-ray analysis. The results obtained are shown in Table 4 below.

TABLE 4

| Sample No. | Measured Light | Edge Effects $(D_1-D_2)/D_1$ | Interimage Effects $(\gamma_R/\gamma_G)$ | $(\gamma_G/\gamma_R)$ | Amount of Residual Silver ($\mu$g/cm²) |
|---|---|---|---|---|---|
| 301** | Blue light | 0.30 | | | |
| | Green light | 0.35 | −0.35 | −0.33 | 0.9 |
| | Red light | 0.39 | | | |
| 302** | Blue light | 0.29 | | | |
| | Green light | 0.34 | −0.30 | −0.29 | 0.5 |
| | Red light | 0.38 | | | |
| 303*** | Blue light | 0.13 | | | |
| | Green light | 0.17 | −0.15 | −0.13 | 5.0 |
| | Red light | 0.19 | | | |
| 304*** | Blue light | 0.10 | | | |
| | Green light | 0.15 | −0.05 | −0.12 | 7.1 |
| | Red light | 0.16 | | | |

**Invention
***Comparison

It is apparent from the results shown above that Samples 301 and 302 which contain Compounds (23) and (26) of the present ivention, respectively, show greater edge effects and interlayer effects as compared with Samples 303 and 304 which contain Comparison Compounds D-5 and D-6, respectively, even though the amount of Compound (23) or (26) was smaller than that of Comparison Compound D-5 or D-6. Further, according to the present invention, the amount of residual silver present is extremely small and thus color turbidity due to insufficient bleaching of silver was prevented.

Furthermore, these samples were cut into films of 35 mm size and photographed to form negative films. Color prints were prepared by printing the negative films using an enlarging technique. The color prints obtained using Samples 301 and 302 had a fine graininess and a sharp image and showed clear colors, particularly clearly reproduced green and red colors in comparison with those obtained using Samples 303 and 304.)

These results indicated that Compounds (23) and (26) provided excellent characteristics in terms of improving graininess, sharpness and color reproduction.

EXAMPLE 4

Sample 401 having the layer structure as shown in FIG. 1 was prepared as follows. In a red-sensitive silver iodobromide emulsion (AgI: 7 mol%) which was spectrally sensitized using Sensitizing Dyes I and II described in Example 1 in the same amount as in Example 1 based on the amount of silver halide, 1-hydroxy-4-chloro-2-n-dodecylnaphthamide was emulsified and mixed as a cyan coupler in an amount of 0.1 mol per mol of silver. In a green-sensitive silver iodobromide emulsion (AgI: 6 mol%) which was spectrally sensitized using Sensitizing Dyes III and IV described in Example 1 in the same amount as in Example 1 based on the amount of silver halide, 1-(2,4,6-trichlorophenyl)-3-[3-(2,4-di-tert-amylphenoxyacetamido)benzamido)]-5-pyrazolone was emulsified and mixed as a magenta coupler in an amount of 0.1 mol per mol of silver. In a blue-sensitive silver iodobromide emulsion (AgI: 6 mol%), α-pivaloyl-α-[4-(4-benzyloxysulfonyl)phenoxy]-2-chloro-5-[γ-(2,4-di-tert-amylphenoxy)-butyramido]acetanilide was emulsified and mixed as a yellow coupler in an amount of 0.25 mol per mol of silver. These emulsions were coated on a cellulose triacetate film support each in a silver coated amount of 1.5 g/m² to prepare a color reversal photographic light-sensitive material 401.

Additionally, in the emulsification of each coupler, dibutyl phthalate and tricresyl phosphate were used as a solvent for the couplers, sorbitan monolaurate and sodium dodecylbenzenesulfonate were used as an emulsifier.

With Sample 401, an antihalation layer containing 300 mg/m² of black colloidal silver and a gelatin intermediate layer of a thickness of 3 mµ were provided under the red-sensitive emulsion layer, a filter layer of yellow colloidal silver (300 mg/m²) was provided between the green-sensitive emulsion layer and the blue-sensitive emulsion layer, an intermediate layer comprising gelatin containing dispersed therein di-tert-amylhydroquinone was provided between the green-sensitive emulsion layer and the red-sensitive emulsion layer, and a protective layer mainly comprising gelatin of a thickness of 3 mµ was provided on the blue-sensitive emulsion layer.

A gelatin hardener and a surface active agent as described in Example 1 were added to each layer.

The coated silver amount of the red-sensitive emulsion layer was 1.5 g/m², that of the green-sensitive emulsion layer was 1.5 g/m², and that of the blue-sensitive emulsion layer was 0.9 g/m².

The molar ratios of silver/coupler in each emulsion layer were 8.0 in the red-sensitive emulsion layer, 9.5 in the green-sensitive emulsion layer and 5.0 in the blue-sensitive emulsion layer.

SAMPLES 402 to 404

Samples 402 to 404 were prepared in the same manner as Sample 401 except that the compounds shown in Table 5 were additionally dissolved in the coupler solvents used for the cyan coupler and the magenta coupler, emulsified, and added to the red-sensitive emulsion layer and the green-sensitive emulsion layer, respectively, of Sample 401.

Samples 401 to 404 thus-prepared were stepwise exposed (20 CMS) to red light and then uniformly exposed (20 CMS) to green light so as to provide a color density of 70% of the maximum color density obtained by color development of the green-sensitive emulsion layer and subjected to the color reversal processing as shown in the following.

| Processing Step | Temperature (° C) | Time (min) |
|---|---|---|
| First Development (black-and-white) | 30 | 24 5 |
| Stopping Bath | " | 1 |
| Washing | " | 2 |
| Fogging Bath | " | 2 |
| Color Development | " | 7 |
| Stopping Bath | " | 2 |
| Hardening Bath | " | 2 |
| Washing | " | 2 |
| Bleaching Bath | " | 4 |
| Washing | " | 2 |
| Fixing Bath | " | 4 |
| Washing | " | 2 |
| Drying | " | |

| Composition of the First Developer Solution | |
|---|---|
| Sodium Sulfite | 60.0 g |
| 1-Phenyl-3-pyrazolidone | 0.3 g |
| Hydroquinone | 5.0 g |
| Sodium Carbonate (monohydrate) | 41.0 g |
| Potassium Bromide | 2.0 g |
| Potassium Iodide (1% aq. soln.) | 1.0 ml |
| Potassium Thiocyanate (1N aq. soln.) | 10.0 ml |
| Sodium Hydroxide (10% aq. soln.) | 2.0 |
| Water to make | 1.0 l |
| Composition of Stopping Solution | |
| Sodium Acetate | 30 g |
| Glacial Acetic Acid | 8 ml |
| Water to make | 1.0 l |
| Composition of Fogging Bath | |
| Sodium Hydroxide | 2.0 g |
| Sodium Borohydride | 0.1 g |
| Water to make | 1.0 l |
| Composition of Color Developer Solution | |
| Benzyl Alcohol | 5.0 ml |
| Sodium Hydroxide | 0.5 g |
| Diethylene Glycol | 3.0 ml |
| Sodium Hexametaphosphate | 2.0 g |
| Sodium Sulfite | 2.0 g |
| Potassium Bromide | 2.0 g |
| 4-Amino-3-methyl-N-ethyl-β-hydroxyethylaniline Sesquisulfate (monohydrate) | 5.0 g |
| Citrazinic Acid | 0.4 g |
| Metaboric Acid | 0.5 g |
| Borax | 77.0 g |
| Water to make | 1.0 l |
| Composition of Hardening Bath | |
| Sodium Hexametaphosphate | 1.0 g |
| Borax (hexahydrate) | 20.0 g |
| Formaldehyde (37% aq. soln.) | 10.0 ml |
| Water to make | 1.0 l |
| Composition of Bleaching Solution | |
| Iron (III) Sodium Ethylenediaminetetraacetate (dihydrate) | 30.0 g |
| Potassium Bromide | 50.0 g |
| Disodium Ethylenediaminetetraacetate | 5.0 g |
| Boric Acid | 3.0 g |
| Borax | 1.5 g |
| Water to make | 1.0 l |
| Composition of Fixing Solution | |
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1.0 l |

Figure 2:
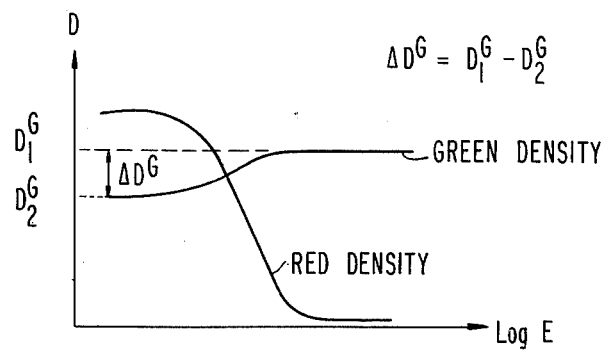

The optical densities and the difference of green density $\Delta D^G$ of the samples thus-processed was determined as shown in FIG. 2. The results obtained are shown in Table 5. The value of $\Delta D^G$ is plus and a larger numerical value means larger interlayer effects.

TABLE 5

| Sample | Compound | | Amount | Interlayer Effects |
|---|---|---|---|---|
| No. | Layer Added | Compound | (mol%) | $\Delta D^G$ |
| 401* | GL | — | — | −0.15 |
| | RL | — | | |
| 402** | GL | Compound (8) | 3 | 0.18 |
| | RL | " | 6 | |
| 403** | GL | Compound (2) | 3 | 0.16 |
| | RL | " | 6 | |
| 404*** | GL | Compound D-2 | 10 | −0.02 |
| | RL | " | 20 | |

*Control
**Present Invention
***Comparison

As can be clearly understood from the results in Table 5, Samples 402 and 403 containing Compounds (8) and (2) of the present invention, respectively, show greater interlayer effects in comparison with Sample 404 containing Comparison Non-Color Forming Coupling Compound D-2.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising a support having thereon at least one silver halide emulsion layer containing a coupling compound which forms a colorless compound with oxidized developer, said coupling compound being represented by the following general formula (I):

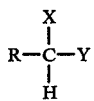

(I)

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO$_2$R$_2$ group in which R$_2$ represents an alkyl group, an aryl group, a pyridine group, a furan group, a thiophene group, a phthalimide group, a succinimide group or Y;
X represents

wherein R$_1$ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting of a benzyloxy group or a thiazolinylidenamino group represented by the following general formula (IV):

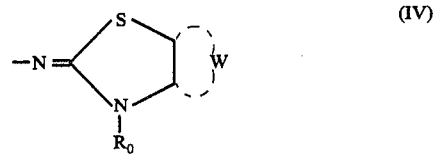

(IV)

wherein W represents a condensed aromatic ring which is unsubstituted or substituted with one or more of an alkyl group, an alkoxy group or a halogen atom; and R$_0$ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

2. The photographic light-sensitive material as claimed in claim 1, wherein Y represents a 5- or 6-benzyloxybenzotriazolyl group, a 5- or 6-(3-methylbenzothiazolinyliden)aminobenzotriazolyl group, a 5- or 6-(3-ethylbenzothiazolinyliden)aminobenzotriazolyl group, a 5- or 6-(3-benzylbenzothiazolinyliden)aminobenzotriazolyl group or a quinoxalino[2,3-f]benzotriazolyl group.

3. The photographic light-sensitive material as claimed in claim 1, wherein Y represents a 3,5-di-(3-methylbenzothiazolinylinden)amino-1,2,4-triazolyl group.

4. The photographic light-sensitive material as claimed in claim 1, wherein said coupling compound is present in an amount of from about 0.0005 to about 0.5 mol per mol of silver halide present in the emulsion layer.

5. A multilayer color photographic light-sensitive material comprising a support having thereon at least one blue-sensitive silver halide emulsion layer containing a yellow color-forming coupler, at least one green-sensitive silver halide emulsion layer containing a magenta color-forming coupler and at least one red-sensitive silver halide emulsion layer containing a cyan color-forming coupler and said material having at least one silver halide emulsion layer containing a coupling compound which forms a colorless compound with oxidized developer, said coupling compound being represented by the following general formula (I):

(I)

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO$_2$R$_2$ group in which R$_2$ represents an alkyl group, an aryl group, a pyridine group, a furan group, a thiophene group, a phthalimide group, a succinimide group or Y;

X represents

wherein R$_1$ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting of a benzyloxy group or a thiazolinylidenamino group represented by the following general formula (IV):

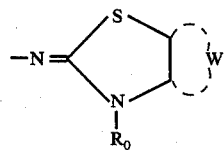

wherein W represents a condensed aromatic ring which is unsubstituted or substituted with one or more of an alkyl group, an alkoxy group or a halogen atom; and R$_0$ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

6. A photographic silver halide emulsion containing a coupling compound which forms a colorless compound with oxidized developer, said coupling compound being represented by the following general formula (I)

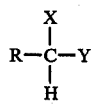

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO$_2$R$_2$ group in which R$_2$ represents an alkyl group, an aryl group, a pyridine group, a furan group, a thiophene group, a phthalimide group, a succinimide group or Y;

X represents

wherein R$_1$ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting of a benzyloxy group or a thiazolinylidenamino group represented by the following general formula (IV):

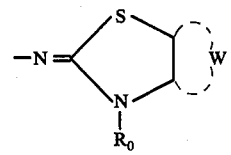

wherein W represents a condensed aromatic ring which is unsubstituted or substituted with one or more of an alkyl group, an alkoxy group or a halogen atom; and R$_0$ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

7. A photographic color developer solution containing a coupling compound which forms a colorless compound with oxidized developer, said coupling compound being represented by the following general formula (I):

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO$_2$R$_2$ group in which R$_2$ represents an alkyl group, an aryl group, a pyridine group, a furan group, a thiophene group, a phthalimide group, a succinimide group or Y;

X represents

wherein R₁ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting of a benzyloxy group or a thiazolinylidenamino group represented by the following general formula (IV):

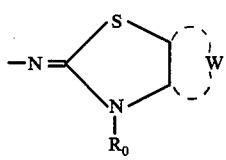

wherein W represents a condensed aromatic ring which is unsubstituted or substituted with one or more of an alkyl group, an alkoxy group or a halogen atom; and R₀ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

8. A method of forming a photographic image comprising developing an imagewise exposed photographic light-sensitive material in the presence of a coupling compound which forms a colorless compound with oxidized developer, said coupling compound being represented by the following general formula (I):

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO₂R₂ group in which R₂ represents an alkyl group, an aryl group, a pyridine group, a furan group, a thiophene group, a phthalimide group, a succinimide group or Y;

X represents

wherein R₁ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting of a benzyloxy group or a thiazolinylidenamino group represented by the following general formula (IV):

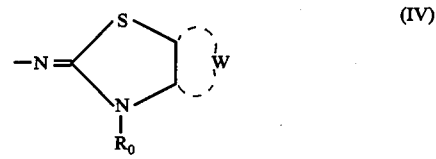

wherein W represents a condensed aromatic ring which is unsubstituted or substituted with one or more of an alkyl group, an alkoxy group or a halogen atom; and R₀ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

9. A method of forming a color photographic image comprising developing a multilayer color photographic light-sensitive material comprising a support having thereon at least one blue-sensitive silver halide emulsion layer containing a yellow color-forming coupler, at least one green-sensitive silver halide emulsion layer containing a magenta color-forming coupler and at least one red-sensitive silver halide emulsion layer containing a cyan color-forming coupler and said material having at least one silver halide emulsion layer containing a coupling compound which forms a colorless compound with oxidized developer, said coupling compound being represented by the following general formula (I):

wherein
R represents a hydrogen atom; an alkyl group; an aryl group; a halogen atom; an —O—Z group in which Z represents an alkyl group, an aryl group, a 5- or 6-membered heterocyclic group containing one or more nitrogen, oxygen or sulfur atoms as a hetero atom, an acyl group or an —SO$_2$R$_2$ group in which R$_2$ represents an alkyl group, an aryl group, a pyridine group, a furan group, a thiophene group, a phthalimide group, a succinimide group or Y;

X represents

wherein R$_1$ represents an aryl group which is unsubstituted or substituted with one or more monovalent substituents selected from the group consisting of a halogen atom, a nitro group, a cyano group, a thiocyano group, a hydroxy group, an alkoxy group, an aryloxy group, an alkyl group, an alkenyl group, an aryl group, an amino group, a carboxy group, an acyl group, an alkoxycarbonyl group, an aryloxycarbonyl group, a carbamoyl group, an acylamino group, a sulfo group, an alkylsulfonyl group, an arylsulfonyl group, an alkoxysulfonyl group, an aryloxysulfonyl group, a sulfamoyl group, a sulfonamido group and a divalent substituent forming a condensed ring with said aryl group; and Y represents (i) a benzotriazolyl group substituted with one or more substituents selected from the group consisting a benzyloxy group or a thiazolinylidenamino group represented by the following general formula (IV):

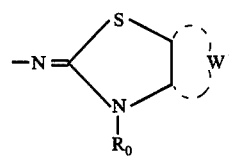

wherein W represents a condensed aromatic ring which is unsubstituted or substituted with one or more of an alkyl group, an alkoxy group or a halogen atom; and R$_O$ represents an aliphatic group or an aryl group, or (ii) a 1,2,4-triazolyl group substituted with a thiazolinylidenamino group of general formula (IV) defined above, wherein said benzotriazolyl group or 1,2,4-triazolyl group represented by Y is bonded to the coupling position of said coupler through the nitrogen atom at the 1-position of the triazole ring thereof.

10. The material of claim 1 wherein (a) R$_1$, if said aryl group, is a substituted or unsubstituted henyl group; (b) R is a hydrogen atom; and Y represents (i) a benzotriazolyl group substituted with one or more substituents selected from the group consisting of a benzyloxy group or a thiazolinylidenamino group represented by the following general formula (IV):

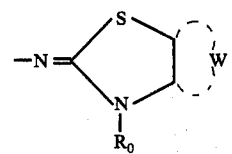

wherein W represents a condensed aromatic ring which can be substituted with one or more of an alkyl group, an alkoxy group or a halogen atom.

11. The material of claim 5 wherein (a) R$_1$, if said aryl group, is a substituted or unsubstituted phenyl group;

(b) R is a hydrogen atom; and Y represents (i) a benzotriazolyl group substituted with one or more substituents selected from the group consisting of a benzyloxy group or a thiazolinylidenamino group represented by the following general formula (IV):

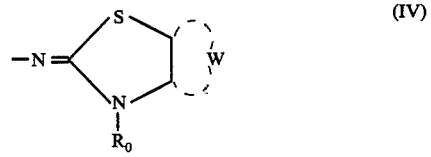

wherein W represents a condensed aromatic ring which can be substituted with one or more of an alkyl group, an alkoxy group or a halogen atom.

12. The emulsion of claim 10 wherein (a) R$_1$, if said aryl group, is a substituted or unsubstituted phenyl group; (b) R is a hydrogen atom; and Y represents (i) a benzotriazolyl group substituted with one or more substituents selected from the group consisting of a benzyloxy group or a thiazolinylidenamino group represented by the following general formula (IV):

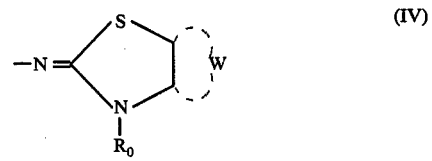

wherein W represents a condensed aromatic ring which can be substituted with one or more of an alkyl group, an alkoxy group or a halogen atom.

13. The developing solution of claim 7 wherein (a) R$_1$, if said aryl group, is a substituted or unsubstituted phenyl group; (b) R is a hydrogen atom; and Y represents (i) a benzotriazolyl group substituted with one or more substituents selected from the group consisting of a benzyloxy group or a thiazolinylidenamino group represented by the following general formula (IV):

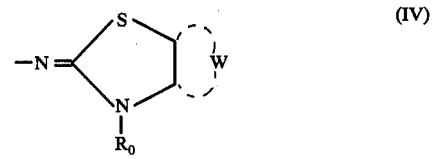

wherein W represents a condensed aromatic ring which can be substituted with one or more of an alkyl group, an alkoxy group or a halogen atom.

14. The method of claim 8 wherein (a) R$_1$, if said aryl group, is a substituted or unsubstituted phenyl group; (b) R is a hydrogen atom; and Y represents (i) a benzotriazolyl group substituted with one or more substituents selected from the group consisting of a benzyloxy group or a thiazolinylidenamino group represented by the following general formula (IV):

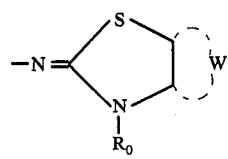

wherein W represents a condensed aromatic ring which can be substituted with one or more of an alkyl group, an alkoxy group or a halogen atom.

15. The method of claim 9 wherein (a) $R_1$, if said aryl group, is a substituted or unsubstituted phenyl group; (b) R is a hydrogen atom; and Y represents (i) a benzotriazolyl group substituted with one or more substituents selected from the group consisting of a benzyloxy group or a thiazolinylidenamino group represented by the following general formula (IV):

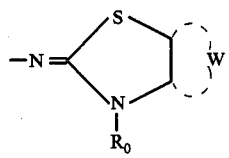

wherein W represents a condensed aromatic ring which can be substituted with one or more of an alkyl group, an alkoxy group or a halogen atom.

16. The material of claim 1 wherein Z, if a hetero group, represents a pyridine group, a furan group, a phthalimide group or a succinimide group.

17. The material of claim 5, wherein Z, if a hetero group, represents a pyridine group, a furan group, a phthalimide group or a succinimide group.

18. The emulsion of claim 6 wherein Z, if a hetero group, represents a pyridine group, a furan group, a phthalimide group or a succinimide group.

19. The developer solution of claim 7 wherein Z, if a hetero group, represents a pyridine group, a furan group, a phthalimide group or a succinimide group.

20. The method of claim 8 wherein Z, if a hetero group, represents a pyridine group, a furan group, a phthalimide group or a succinimide group.

21. The method of claim 9 wherein Z, if a hetero group, represents a pyridine group, a furan group, a phthalimide group or a succinimide group.

22. The material of claim 1 wherein $R_0$ is an alkyl group having 1 to 4 carbon atoms.

23. The material of claim 5 wherein $R_0$ is an alkyl group having 1 to 4 carbon atoms.

24. The emulsion of claim 6 wherein $R_0$ is an alkyl group having 1 to 4 carbon atoms.

25. The developer solution of claim 7 wherein $R_0$ is an alkyl group having 1 to 4 carbon atoms.

26. The method of claim 8 wherein $R_0$ is an alkyl group having 1 to 4 carbon atoms.

27. The method of claim 9 wherein $R_0$ is an alkyl group having 1 to 4 carbon atoms.

28. The material of claim 1 wherein Y is

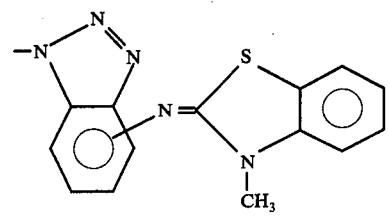

29. The material of claim 5 wherein Y is

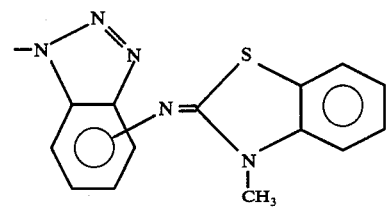

30. The emulsion of claim 6 wherein Y is

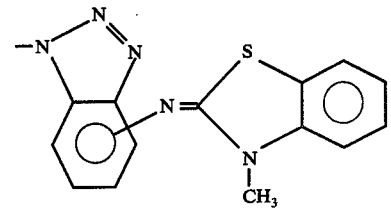

31. The developing solution of claim 7 wherein

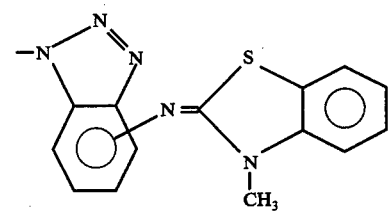

32. The method of claim 8 wherein Y is

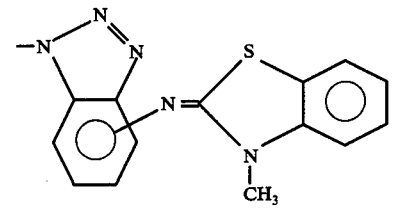

33. The method of claim 9 wherein y is

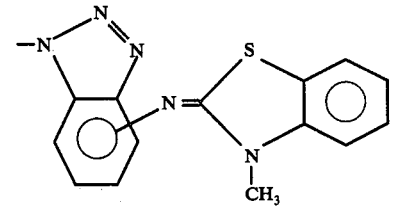

* * * * *